United States Patent [19]
Dupuis et al.

[11] Patent Number: 5,935,896
[45] Date of Patent: Aug. 10, 1999

[54] CATALYST SUPPORTS AND CATALYSTS FOR DEHYDROCYANATION REACTIONS AND PROCESSES FOR PRODUCING THEM

[75] Inventors: Jacques Dupuis; Peter Trübenbach, both of Ludwigshafen; Ekkehard Schwab, Neustadt; Michael Kröner, Bergholz-Rehbrücke, all of Germany

[73] Assignee: BASF Aktiengesellschaft, Ludwigshafen, Germany

[21] Appl. No.: 08/845,436

[22] Filed: Apr. 25, 1997

[30] Foreign Application Priority Data

May 2, 1996 [DE] Germany .............................. 196 17 530
May 6, 1996 [DE] Germany .............................. 196 18 129

[51] Int. Cl.$^6$ ..................................... B01J 21/04
[52] U.S. Cl. .......................... 502/439; 502/243; 502/250; 502/414; 502/415
[58] Field of Search ..................................... 502/304, 314, 502/315, 318, 370, 331, 337, 323, 346, 415, 439, 527, 250, 243; 423/213.2, 213.5

[56] References Cited

U.S. PATENT DOCUMENTS

| | | | |
|---|---|---|---|
| 4,025,457 | 5/1977 | Tomita et al. ........................... | 252/373 |
| 4,297,512 | 10/1981 | Mainusch et al. ....................... | 564/490 |
| 4,366,093 | 12/1982 | Shiozaki et al. ......................... | 252/477 |
| 4,711,930 | 12/1987 | Hoelderich et al. .................... | 502/209 |
| 4,722,920 | 2/1988 | Kimura et al. .......................... | 502/439 |
| 4,859,642 | 8/1989 | Hoelderich et al. ....................... | 502/2 |
| 5,145,900 | 9/1992 | Sterzel et al. ........................... | 524/404 |
| 5,262,130 | 11/1993 | Kissel et al. ............................. | 422/311 |
| 5,534,475 | 7/1996 | Cardinas et al. ........................ | 502/304 |

FOREIGN PATENT DOCUMENTS

| | | |
|---|---|---|
| 206 193 | 6/1986 | European Pat. Off. . |
| 208 929 | 1/1987 | European Pat. Off. . |
| 3443463 | 11/1984 | Germany . |
| 3521766 | 6/1985 | Germany . |
| 19533484 | 9/1995 | Germany . |
| 19533486 | 9/1995 | Germany . |

OTHER PUBLICATIONS

English language Abstract of DE 19533484, Sep. 12, 1995.

*Primary Examiner*—Shailendra Kumar
*Attorney, Agent, or Firm*—Keil & Weinkauf

[57] ABSTRACT

An $SiO_2$-free, $\alpha Al_2O_3$-containing catalyst support in the form of a hollow body in which at least part of the outer walls of the hollow body is open can be used to produce a catalyst for dehydrocyanation reactions.

5 Claims, 1 Drawing Sheet

CATALYST SUPPORTS AND CATALYSTS FOR DEHYDROCYANATION REACTIONS AND PROCESSES FOR PRODUCING THEM

The present invention relates to an $SiO_2$-free, $\alpha$-$Al_2O_3$-containing catalyst support in the form of a hollow body, wherein at least part of the outer walls of the hollow body is open. In addition, the present invention relates to a process for producing the support, a catalyst which includes the above support, its production and the use of the catalyst for dehydrocyanation reactions.

BACKGROUND OF THE INVENTION

DE-A-195 33 486 and DE-A-195 33 484 disclose catalyst supports or catalysts having a complex shape and processes for producing them, these catalyst supports or catalysts having a narrow monomodal or polymodal pore size distribution.

N-Vinylformamide is prepared by thermal dehydrocyanation of N-formylalanine nitril using a catalyst based on $Al_2O_3$. The catalyst used hitherto was produced by impregnation of an $Al_2O_3$ catalyst support with an active component and subsequent drying. Catalyst geometries which have been used hitherto are rings, wagon wheels and honeycombs. $SiO_2$ was sometimes added to increase the mechanical strength of the $Al_2O_3$ catalyst support. Thus, EP-A-0 206 193 (or DE-A 35 21 766) describes a honeycomb catalyst containing as main constituents from 30 to 95% by weight of an iron compound, calculated as $Fe_2O_3$, and from 0.1 to 60% by weight of an aluminum, cerium and/or chromium compound, calculated as $Al_2O_3$, $CeO_2$, $Cr_2O_3$, and/or from 1 to 50% by weight of an alkali metal compound, and also the use of this catalyst as a dehydrocyanation catalyst.

EP-A-0 208 929 concerns a catalyst fixed bed structure using the catalyst described in the above-cited applications for exothermic and endothermic chemical reactions having a high heat of reaction.

DE-A 34 43 463 relates to a process for preparing N-vinylformamide by pyrolysis of formylalanine nitril in the presence of solids as catalysts, these catalysts comprising alkali metal carbonates and alkaline earth metal carbonates, magnesium oxide, calcium oxide and barium oxide and particularly advantageous catalysts comprising alkali metal carbonates and/or alkaline earth metal carbonates on a-aluminum oxide as support.

During the catalytic synthesis of N-vinylformamide from N-formylalanine nitril, the active components such as alkali metal compounds and/or alkaline earth metal compounds gradually react with $SiO_2$ at from 300° C. to 600° C. to give alkali metal and/or alkaline earth metal silicates which are inactive in respect of the reaction to be catalyzed and whose increasing formation reduces the mechanical strength of the catalyst. Accordingly, when the $SiO_2$-containing catalysts customarily employed are used, active component is continually lost during the reaction and, furthermore, the stability of the catalyst is reduced as the reaction progresses.

Extrusion enables $SiO_2$-free tubes or wagon wheel profiles to be produced. Previously, only $SiO_2$-containing shaped bodies could be produced by pressing, since the $SiO_2$-free pressed aluminum oxide bodies disintegrate after centering owing to their relatively low mechanical strength. Accordingly, without subsequent machining, only simple geometries of $SiO_2$-free $Al_2O_3$ shaped bodies were obtainable in tube or rod form by means of extrusion. The use of simple catalyst geometries results, owing to unfavorable flow through the reactor bed, in high pressure drops and consequently unsatisfactory throughputs in catalytic reactions such as dehydrocyanation reactions.

In the case of the strongly exothermic reactions, it is also important for a high heat input into the catalyst bed to be ensured. In the case of reactions at subatmospheric pressure, the heat input is achieved predominantly by heat radiation and not by heat conduction. However, customary geometries of catalyst supports, eg. rings, wagon wheels and honeycombs, represent obstacles for heat transfer by radiation.

BRIEF SUMMARY OF THE INVENTION

It is an object of the present invention to provide an $SiO_2$-free $\alpha$-$Al_2O_3$-containing catalyst support whose use results in a lower pressure drop, a relatively high heat input, no active component loss and no loss of the mechanical stability during the catalytic reaction, in particular in the case of dehydrocyanation reactions.

We have found that this object is achieved by the catalyst support or catalyst of the present invention.

DETAILED DESCRIPTION OF THE INVENTION

As mentioned in the introduction, the present invention provides an $SiO_2$-free, $\alpha$-$Al_2O_3$-containing catalyst support in the form of a hollow body, wherein at least part of the outer walls of the hollow body is open.

The present invention further provides an $SiO_2$-free, $\alpha$-$Al_2O_3$ containing catalyst comprising a catalyst support as defined above and, applied thereto, at least one alkali metal compound or at least one alkaline earth metal compound or a mixture thereof.

The definition of the shape of the catalyst support of the present invention encompasses all hollow bodies such as rings, wagon wheels and honeycombs, and also spheres, cubes, cuboids, cylinders, truncated pyramids and truncated cones, tetrahedra having a truncated point, provided that, according to the present invention, at least part of the outer walls is open.

Preferably, the catalyst support extends along a longitudinal axis and tapers along this axis. It is to be noted here that the openings in the outer walls of the hollow body are preferably oriented parallel to the longitudinal axis. Examples of such tapering shapes are, in particular, a truncated cone, a tetrahedron having a truncated point, a truncated pyramid and shapes similar to a truncated pyramid. For the purposes of the present application, the term "shapes similar to a truncated pyramid" refers to all shapes whose basal and top plates are, unlike a truncated pyramid, not square but rectangular. In its most extreme configuration, the catalyst support having a shape similar to a truncated pyramid can be described by two window frames which are connected to one another by at least three columns, where one of the window frames (basal plate) has a greater edge length than the other (top plate). The shape of the catalyst support is most preferably that of a truncated cone, a truncated pyramid or a shape similar to a truncated pyramid.

Figure 1:
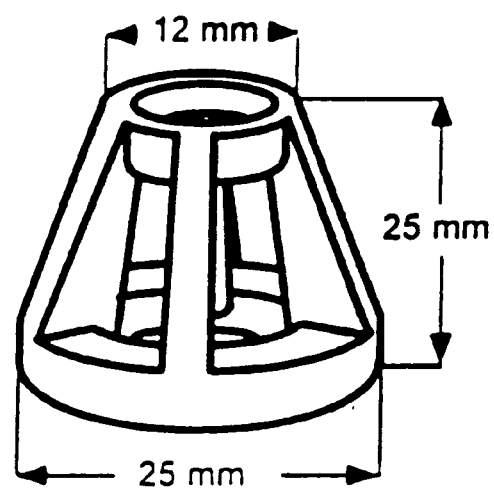
FIGS. 1 and 2 show schematic diagrams of two embodiments of the catalyst supports according to the present invention.

FIG. 1 shows a schematic diagram of the catalyst support of the present invention in the form of a truncated cone. If the two rings are replaced by corresponding square or rectangular basal or top frames, this diagram corresponds to the shapes described for the purposes of the present application as a truncated pyramid or a shape similar to a truncated pyramid.

Particular preference is given to catalyst supports in the form of a truncated cone having the following dimensions:
  a) Basal ring diameter: from about 10 to about 300 mm, preferably from about 10 to about 200 mm, more preferably from about 10 to about 50 mm;
  b) Height: from about 10 to about 300 mm, preferably from about 10 to about 200 mm, more preferably from about 10 to about 50 mm;
  c) Top ring diameter: from about 5 to about 150 mm, preferably from about 5 to about 100 mm, more preferably from about 5 to about 30 mm;
  d) Number of columns connecting the basal and top rings: from 3 to 12, with the number of columns depending on the diameter of the basal and top rings and being 3 or 4 in the case of base diameters of from 10 to 50 mm, from 3 to 6 in the case of basal ring diameters of from about 20 to about 100 mm and from 3 to 12 in the case of diameters of from about 100 to 300 mm, where the diameter of the columns is generally from about 0.5 to about 50 mm and the diameter of the columns of course depends on the size of the basal and top rings;

and catalyst supports in the form of a truncated pyramid having the following dimensions:
  a) Edge length of the basal plate: from about 7 to about 200 mm, preferably from about 7 to about 150 mm, more preferably from about 7 to about 40 mm;
  b) Height: From about 10 to about 300 mm, preferably from about 10 to about 200 mm, more preferably from about 10 to about 50 mm;
  c) Edge length of the top plate: from about 5 to about 150 mm, preferably from about 5 to about 100 mm, more preferably from about 5 to about 25 mm;
  d) Number of columns connecting the basal and top plates: from 3 to 12, with the number of columns depending on the edge length of the basal and top plates and being 3 or 4 in the case of basal edge lengths of from about 10 to about 50 mm, from 3 to 6 in the case of basal edge lengths of from about 20 to about 100 mm and from 3 to 12 in the case of basal edge lengths of from about 100 to about 300 mm, where the diameter of the columns is generally from about 0.5 to about 50 mm and the diameter of the columns of course depends on the size of the basal and top plates.

The diameter of the above-described columns is preferably from about 0.5 to 30 mm, more preferably from about 0.5 to 20 mm.

Although the ratio of the diameters of basal and top rings or the edge lengths of basal and top plates is subject to no particular restrictions, the ratio of the diameter or edge length of the basal ring or plate to the dimensions of the corresponding top ring or plate is preferably about 2:1.

It is to be mentioned that the columns may be constructed in the form of a rod or a staircase comprising one or mor steps.

The present invention also provides an $SiO_2$-free, $\alpha$-$Al_2O_3$-containing catalyst comprising a catalyst support as mentioned above and, applied thereto, at least one alkali metal compound or at least one alkaline earth metal compound or a mixture thereof.

Alkali metal salts or alkaline earth metal salts which can be used for applying the active components to the catalyst support of the present invention are, in principle, all water-soluble alkali metal and/or alkaline earth metal salts. However, preference is given to using the carbonates and acetates such as sodium carbonate, potassium carbonate, magnesium carbonate, strontium carbonate, barium carbonate, marble, dolomite, chalk, magnesite and calcium acetate, and mixtures thereof. Particular preference is given to using potassium carbonate.

On drying the catalyst, these alkaline metal and/or alkaline earth metal salts are converted into the corresponding oxides and/or carbonates.

The specific surface areas by the BET method of the catalyst supports and catalysts of the present invention are generally from about 0.01 to about 100 $m^2/g$, preferably from about 0.1 to about 50 $m^2/g$, more preferably from about 0.5 to about 10 $m^2/g$ and in particular from about 1 to about 8 $m^2/g$.

Of course, the catalyst supports and catalysts can also be coated with inorganic powders or powder mixtures by bicoating, which enable specific surface areas of over 100 $m^2/g$ to be achieved.

The pore size distribution within the catalyst support of the present invention or the catalyst of the present invention is monomodal or polymodal, i.e. bimodal, trimodal, tetramodal or higher-modal, preferably monomodal or bimodal, more preferably monomodal, with the mean pore diameter being from about 0.01 to about 10.0 $\mu$m, preferably from about 0.05 to 1.0 $\mu$m, more preferably from about 0.1 to about 0.8 $\mu$m, in each case measured using the Hg pressure porosymmetry method.

The catalyst supports in question can be produced in one shaping step by pressing or, in particular, by injection molding without subsequent machining. The process of the present invention makes it possible to produce these catalyst supports in $SiO_2$-free form while maintaining sufficient mechanical stability. The catalyst supports consisting of pure, i.e. at least 95%, $Al_2O_3$ do not, after impregnation with the active component, suffer from active component loss resulting from silicate formation, do not display degradation of the mechanical stability and therefore allow higher operating lives with higher throughputs.

The present invention accordingly also provides a process for producing a catalyst support which comprises the following steps:
I) Shaping a mixture comprising
  (A) a powder having an $\alpha$-$Al_2O_3$ content of at least 95% by weight and
  (B) a polymeric binder,
II) Removing the polymeric binder (B), and
III) Presintering the shaped body obtained from step (II)

The mixture shaped in step (I) preferably additionally contains as component
  (C) a dispersant which is removed in step (II) or (III).

The invention also provides a process for producing a catalyst which comprises, in addition to the steps I) to III) as defined above, the step
IV) Impregnating the shaped body obtained from step (III) with at least one solution of at least one alkali metal salt or at least one alkaline earth metal salt or a mixture thereof and subsequently drying the catalyst obtained, and also an $SiO_2$-free, $\alpha$-$Al_2O_3$-containing catalyst comprising a catalyst support and at least one alkali metal compound or at least one alkaline earth metal compound or a mixture thereof, which catalyst is obtainable by a process comprising the following steps:
I) Shaping a mixture comprising
  (A) a powder having an $\alpha$-$Al_2O_3$ content of at least 95% by weight and (B) a polymeric binder, II) Removing the polymeric binder (B), III) Presintering the shaped body obtained from step (II), and IV) Impregnating the shaped body obtained from step (III) with at least one solution of at least one alkali metal salt or at least one alkaline earth metal salt or a mixture thereof and subsequently drying the catalyst obtained.

The process of the present invention for producing a catalyst support (leaving out the step IV) or the catalyst is preferably carried out as follows:

I) Shaping a mixture comprising (A) from 50 to 70% by volume of a powder containing at least 95% by weight of $Al_2O_3$ (B) from 30 to 85% by volume of a polymeric binder which is selected from the group consisting of polyethylene polymers, polypropylene polymers, copolymers of ethylene, propylene, 1-butene or isobutene, polystyrene copolymers, polymethyl methacrylate copolymers, polyethylene oxide copolymers, ethylvinyl acetate copolymers, and mixtures thereof, and (C) from 0 to 15% by volume of a dispersant, II) Removing the component (B) and, if present, the component (C) by pyrolysis at from 400 to 600° C, III) Presintering at from 600° C. to 1700° C., and IV) Applying an active component by soaking, impregnation or spray impregnation and subsequently drying the catalyst thus obtained.

More preferably, the component (B) used in the above process is a mixture comprising ($B_1$) from 50 to 100% by weight of a polyoxymethylene homopolymer or copolymer and ($B_2$) from 0 to 50% by weight of a polymer which is homogeneously soluble in $B_1$ or can be dispersed to a mean particle size of less that 1 $\mu$m in $B_1$), when this mixture of $B_1$) and $B_2$) is used as component (B), the binder can be removed not only by the above-defined pyrolysis but also by acid-catalyzed binder removal at from 100° C. to 150° C. in an inert gas atmosphere.

In the case of the acid-catalyzed removal of the binder component (B), the component (C) is, for the purposes of the process of the present invention, either removed by pyrolysis in an additional step (IIa) or removed pyrolitically at from about 300 to about 600° C. during the heating procedure in the presintering step (III).

The process of the present invention for producing the catalyst support and a catalyst is explained in more detail below, both in respect of the reaction procedure and also the starting materials used.

The shaping step can be carried out as follows:

In a mixing apparatus provided with heating, for example a kneader, an extruder or a shear roller extruder, the component (A) and, if desired, subsequently the dispersant (C) or first component (C) and then component (A) or the components (A) and (C) together can be added to the polymer of component (B) in the molten state from about 80 to about 250° C., preferably from about 100 to about 220° C., more preferably from about 120 to about 200° C. The intensively mixed compositions can be shaped, for example, by extrusion, pressing or injection molding, in particular by injection molding at from about 120 to about 250° C., preferably from about 140 to about 220° C., more preferably from about 150 to about 200° C., and pressures of from about 500 to about 2000 bar, preferably from about 600 to about 1800 bar, more preferably from about 700 to about 1600 bar. In this way, catalyst supports of the type in question having any shape can be produced in one shaping operation at injection molding tool temperatures of from about 40 to about 160° C., preferably from about 60 to about 150° C., more preferably from about 80 to about 140° C., without subsequent machining.

The green bodies obtained after the shaping procedure can be subjected to pyrolysis at from about 300 to about 600° C., preferably from about 350 to about 600° C., more preferably from about 400 to about 600° C., to remove the binder (B) and any dispersants (C) present.

From using the preferred binders $B_1$ and $B_2$ as defined above, these can be removed catalytically in a gaseous, acid-containing atmosphere at from about 100 to about 160° C., preferably at from about 100 to about 150° C., more preferably below the softening temperature of the polyacetal used (components $B_1$ and $B_2$).

The term "gaseous, acid-containing atmosphere" here refers to both pure acids which are gaseous at treatment temperatures and also mixtures of acids with a carrier gas. Suitable carrier gasses are, for example, air or nitrogen or noble gasses.

Suitable acids include inorganic acids which are gaseous at room temperature, for example hydrogen halides, hydrogen sulfides or those acids which can be vaporized to an appreciable degree at the treatment temperatures, e.g. nitric acid.

Suitable organic acids are essentially those acids or acid mixtures which have a boiling point or sublimation point at atmospheric pressure of below 130° C., for example oxalic acid, formic acid, acetic acid or trifluoroacetic acid.

Instead of the gaseous, acid-containing atmosphere, the demolded green bodies can also be treated in an atmosphere containing gaseous boron trifluoride for the purpose of removing the binder. Atmospheres containing gaseous boron trifluoride include both pure boron trifluoride and mixtures of boron trifluoride with a carrier gas. Suitable carrier gasses are, for example, air or nitrogen or noble gasses.

Instead of boron trifluoride, it is naturally also possible to use adducts of boron trifluoride which can, at the treatment temperatures, be edissociated to form the starting components, reversibly and without the decomposition of the components. Particularly suitable are the addition compounds of boron trifluoride with ethers, e.g. dimethyl ether, diethyl ether, dibutyl ether and tert-butyl methyl ether.

Particular preference is given to nitric acid, and hydrous oxalic acid or oxalic acid dihydrate. Glyoxylic acid is also suitable. Other useful acids are benzenesulfonic acid, naphthalene sulfonic acids and maleic acid or mixtures of these. They can be used for the binder removal either on their own or together with a carrier gas, such as air, nitrogen or a noble gas.

To aid metering-in, it can be advantageous to use the abovementioned acids as a solution in polar solvents, preferably having boiling points below 200° C. Suitable solvents are, in particular, water, isopropanol, acetone, dioxane, ethanol, acetic acid and folic acid. The acid-catalyzed binder removal can be carried out at atmospheric pressure or under reduced pressure (from about 0.001 to about 1 bar).

The shaped bodies which have been freed of the binder (B) either by pyrolysis or treatment in a gaseous, acid-containing atmosphere can be sintered in the subsequent presintering step, generally at from about 600 Is to about 1600° C., preferably from about 800 to about 1400° C., more preferably from about 900 to about 1300° C., under oxidizing conditions, i.e. in the presence of air, or an inert gas such as $N_2$ or Ar, or reducing conditions, i.e. in the presence of $N_2$, $H_2$, $Ar/H_2$, to give the catalyst supports having their final strength and pore size distribution.

The sintering process generally considerably increases the stability and hardness of the porous shaped body. The lateral compressive strength of the specimens presintered at about 1100° C. is generally from about 100 to about 1000 N, preferably from about 100 to about 600 N, more preferably from about 200 to about 500 N and in particular from about 250 to about 400 N. The water absorption is generally in the range from about 0.05 to about 5 ml/g, preferably from about 0.1 to about 1 ml/g, more preferably from about 0.1 to about 0.5 ml/g.

The excellent active component absorption enables the catalysts to be readily recycled after use by further impregnation with the active components. Apart from strictly monomodal pore size distributions, it is also possible to produce polymodal (bimodal, trimodal, tetramodal or higher-model) pore size distributions. As indicated above, the shaped bodies which have been freed of the binder (B) are only presintered i.e. the sintering process is stopped at the desired degree of porosity, i.e. the desired specific surface area, before full sintering which results in very dense, nonporous shaped bodies.

The mean pore size is generally determined by the particle size of the component (A), i.e. only by the spaces in between the powder particles used. The mean pore size and the pore size distribution are therefore dependent on the mean particle size and the particle size distribution of the powder used. In this way, commercially available ceramic powders make it possible to produce mechanically stable, crack-free, monomodally or polymodally porous materials such as the catalyst supports or catalysts of the present invention. The narrow pore size distribution can thus be adjusted as necessary in the mesopore and micropore range and generally leads to a highly monodisperse pore size distribution.

The mean particle size of the powder of the component (A) used according to the present invention is generally from about 0.01 to about 500 $\mu$m, preferably from about 0.3 to about 100 $\mu$m, more preferably from about 0.5 to about 10 $\mu$m.

The catalyst support or catalyst of the present invention has the advantage that it is essentially free of micropores. By-products are frequently formed in the micropores since there the residence time of the starting materials is greater than in the mesopores or micropores. α-aluminum oxide suitable as component (A) has a content of pure α-aluminum oxide of from about 95 to 100% by weight. The $\alpha Al_2O_3$ used can contain up to 5% of dopants. Dopants which may be mentioned are: oxides of the elements potassium, rubidium, cesium, magnesium, calcium, strontium, barium, titanium, vanadium, chromium, manganese, iron, cobalt, nickel, copper, zinc, zirconium, niobium, molybdenum, ruthenium, rhodium, palladium, silver, cadmium, hafnium, tantalum, tungsten.

As component (B), preference is given to using the following:
Polyethylene polymers, polypropylene polymers, copolymers or ethylene, propylene, 1-butene or isobutene, polystyrene copolymers, ethylvinyl acetate copolymers, mixtures of
$B_1$) from 50 to 100% by weight, preferably from 70 to 90% by weight, more preferably from 80 to 88% by weight, of a polyoxymethylene homopolymer of copolymer, as are known from EP-A-444 475, and
$B_2$) from 0 to 50% by weight, preferably from 10 to 30% by weight, more preferably from 12 to 25% by weight, of a polymer homogeneously dissolved in $B_1$) or dispersed to a mean particle size of less than 1 $\mu$m in $B_1$), preferably poly-1,3-dioxolane, poly-1,3-dioxane, poly-1,3-dioxepane, particularly preferably poly-1,3-dioxepane.

The organic binder can also be a mixture of one or more thermoplastic resins such as polyacetal, polyethylene, polypropylene, polystyrene, polymethyl methacrylate and one or more plasticisers such as polyethylene glycol, polypropylene glycol, polybutanediol formal, phthalic esters, ethylene vinyl acetate copolymers and montan ester waxes.

Suitable polyacetal binders are, for example, polyoxymethylene which preferably has a molecular weight of from about 10,000 to about 500,000. Apart from homopolymers of formaldehyde or trioxane, it is also possible to use copolymers of trioxane with, for example, cyclic ethers such as ethylene oxide and 1,3-dioxolane, or formals such as 1,3-dioxepane, 1,3-dioxane or their mixtures, or homopolymers selected from the group consisting of poly-1,3-dioxelane, poly-1,3-dioxane or poly-1,3-dioxepane, with the amounts of the copolymers generally being from about 10 to about 30% by weight of the polymers.

In addition, the organic binders can contain auxiliaries such as thermoplastic binders, e.g. polyethylene, polymethyl methacrylate or polyethylene oxide, and dispersants such as lubricants, e.g. polyethylene glycol, stearic acid, fatty alcohols, polyvinylpyrrolidone or polyvinyl alcohol. The amount of such auxiliaries is generally from about 0.1 to about 12% by weight, based on the total mass.

Suitable components (C) are dispersants as are known from EP-A-444 475. Examples which may be mentioned are organic carboxylic acids, amines, amides or maleimides, stearic acid, polyvinylpyrrolidone, polyvinyl alcohol, polyethylene glycol, polypropylene glycol, polyethylene oxide and montan waxes, preferably organic carboxylic acids, amines, amides or maleimides, polyethylene glycol and polyethylene oxide, particularly preferably organic carboxylic acids, amines, maleimides, polyethylene glycol and polyethylene oxide.

The mixtures used for producing the catalyst support or catalyst of the present invention preferably contain from about 15 to about 70% by weight, more preferably from about 30 to about 70% by weight, in particular from about 50 to about 65% by weight, of the component (A), from about 30 to about 85% by weight, preferably from about 30 to about 70% by weight and in particular from about 35 to about 50% by weight, of the component (B), and from 0 to about 15% by weight, preferably from about 1 to about 12% by weight, in particular from about 2 to about 8% by weight, of the component (C).

In the process of the present invention, the component (A) is generally deagglomerated with the aid of a dispersant (C) and the uniformly sized starting powder particles are thus incorporated into an organic binder (B) at a comparatively high content of component (A). the organic binder fills the generally almost uniform large and regularly arranged spaces between the powder particles. The micropores having a size of about 100 $\mu$m which are present in the starting powder of component (A) as a result of agglomerate formation are generally eliminated by the deagglomeration. After removal of the organic binder and the organic dispersant, if present, strictly uniform-sized pores remain between the powder particles when a powder having a narrow monomodal particle size distribution is used. In general the mean pore diameter is 25% of the mean particle diameter of the powder used. When using powders having a polymodal particle size distribution or when using porous powders, polymodal (bimodal, trimodal, tetramodal or higher-model) pore size distributions can also be produced, with the pore size being determined by the spaces between the powder particles and by the internal porosity of the powder particles.

For further details on the production of catalysts having a specific pore size distribution, reference is made to DE-A-19533486.8 and DE-A19533484.1 of the applicant, the contents of which relating to production of the catalyst are hereby incorporated by reference into the present application.

To produce the catalyst of the present invention, in step (IV) of the above process the catalyst support is impregnated in a manner known per se with water-soluble alkali metal and/or alkaline earth metal salts and the salts are converted into the corresponding carbonates and/or oxides by subsequent thermal treatment, i.e. drying at from about 100° C. to about 400° C., preferably from about 100° C. to about 200° C.

In principle, all water-soluble alkali metal and/or alkaline earth metal salts can be used for the impregnation.

However, preference is given to using carbonates or acetates such as sodium carbonate, potassium carbonate, magnesium carbonate, strontium carbonate, barium carbonate, marble, dolomite, chalk, magnesite and calcium acetate or mixtures thereof.

Furthermore, the present invention provides for the use of the catalyst of the present invention as a dehydrocyanation catalyst, preferably as catalyst for the conversion of N-formylalanine nitrile into N-vinylformamide.

Conclusively, the present invention also relates to a process for the dehydrocyanation of chemical compounds comprising the steps of:

pyrolysing the chemical compound to be dehydrocyanated in the presence of a catalyst according to the invention under reduced pressure and a temperature in the range of 250 to 650° C., cooling the pyrolysis product, and subsequently isolating a desired product, wherein preferably this process is used for converting N-formylalanine nitrile into N-vinylformamide.

The exact process parameters for the thermal dehydrocyanation of N-formylalanine nitrile to give N-vinylformamide are described in DE-A 34 43 463, whose contents are hereby incorporated by reference into the present application.

EXAMPLES

Example 1

1,000 g of α-$Al_2O_3$ powder CT 3000 SG (ALCOA) were kneaded at 180° C. with a binder based on polyacetal, comprising 162 g of a polyoxymethylene copolymer (POM/PBDF) of trioxane and 2.5% by weight of butanediol formal having an average molecular weight of 150,000 and where 41 g of polybutanediol formal having a molecular weight of 50,000 and 50 g of polyethylene glycol having a molecular weight of 800 as auxiliary, and injection molded on an ALLROUNDER 370 C (ARBURG) at a composition temperature of 180° C., an injection pressure of 1,000 bar and a mold temperature of 140° C. to give the catalyst support shown in FIG. 1. These catalyst supports (25 mm×25 mm×12 mm, 4 columns, see FIG. 1) were pyrolyzed at 600° C. for 2 hours under $N_2$ and then presintered for 2 hours at 1,100° C. in air in a muffle furnace.

The following properties were measured on the calcined catalyst supports:

| | |
|---|---|
| - Lateral compressive strength | 298 N (± 77 N) |
| - Water absorption | 0.176 ml/g |
| - BET surface area | 4.49 m²/g |
| - mean pore diameter (by the Hg pressure porosymmetry method) | 0.165 μm |
| - total pore volume (by the Hg pressure porosymmetry method) | 0.185 ml/g |

16 kg of the catalyst supports (25 mm×25 mm×12 mm, 4 columns, see FIG. 1) were impregnated in a pyrolysis reactor (diameter=100 mm, length=3 m) with 10 l of a 40% strength aqueous potassium carbonate solution for 12 hours and dried at 100° C. for 12 hours. The catalysts thus obtained were then tested in the synthesis of N-vinylformamide from N-formylalanine nitrile at 10 mbar and 400° C.

| | |
|---|---|
| Conversion | 93 % |
| Selectivity | 98.8 % |
| Pressure drop | 2 mbar |
| Potassium loss | 25 % (not as silicate) |
| Heat transfer coefficient | 28 W/m²K |
| Radial thermal conductivity | 0.3 W/mK |
| Operating life | >2,000 h |

Example 2

1,000 g of α-$Al_2O_3$ powder were kneaded at 180° C. with a binder based on polyacetal, comprising 162 g of a polyoxymethylene copolymer (POM/PBDF) of trioxane and 2.5% by weight of butanediol formal having an average molecular weight of 150,000 and where 41 g of polybutanediol formal having a molecular weight of 50,000 and 50 g of polyethylene glycol having a molecular weight of 800 as auxiliary, and injection molded on an ALLROUNDER 370 C (ARBURG) at a composition temperature of 180° C., an injection pressure of 1,000 bar and a mold temperature of 140° C. to give the catalyst support shown in FIG. 1.

These catalyst supports (25 mm×25 mm×12 mm, 4 columns, see FIG. 1) were subjected to binder removal for 10 hours in a HERAEUS binder furnace (60 l) using 70 ml/h of a 5% strength by weight solution of oxalic acid in acetic acid (99% pure) or 30 ml/h of 100%-pure nitric acid at 140° C. under an $N_2$ stream of 300 l/h, with the polyoxymethylene being depolymerized to give formaldehyde. The catalyst supports were then calcined in a muffle furnace, first for 2 hours at 600° C. in air and then for 2 hours at 1300° C. in air.

The following properties were measured on the calcined catalyst supports:

| | |
|---|---|
| - Lateral compressive strength | 650 N (± 170 N) |
| - Water absorption | 0.109 ml/g |
| - BET surface area | 2.85 m²/g |
| - mean pore diameter (by the Hg pressure porosymmetry method) | 0.150 μm |
| - total pore volume (by the Hg pressure porosymmetry method) | 0.127 ml/g |

After impregnation and drying of the catalyst supports (25 mm×25 mm×12 mm, 4 columns, see FIG. 1) as in Example 1, the catalysts thus obtained were tested as in Example 1 in respect of their performance in the synthesis of N-vinylformamide from N-formylalanine nitrite.

| Conversion | 91 % |
|---|---|
| Selectivity | 98.7 % |
| Pressure drop | 2 mbar |
| Potassium loss | 25 % (not as silicate) |
| Heat transfer coefficient | 28 W/m²K |
| Radial thermal conductivity | 0.3 W/mK |
| Operating life | >2,000 h |

Comparative Example

Figure 2:
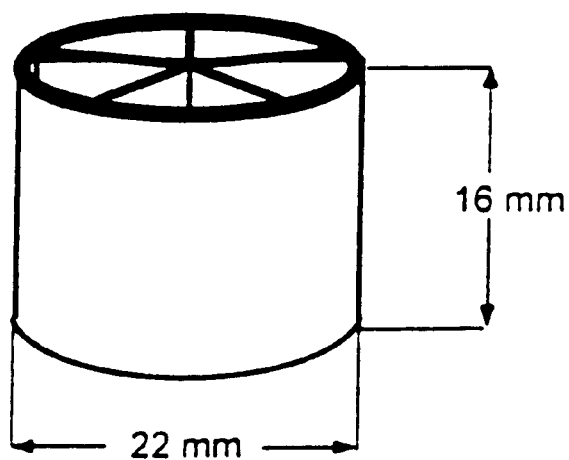

The wagon wheel catalyst supports shown in FIG. 2 were made in a known manner by the extrusion method. To do this, 3,000 g of AlOOH were made into a paste with 150 g of potato starch and 28 g of methyl cellulose and about 1 l of water. After kneading for 3 hours, the plastic mass was extruded and cut to form wagon wheel catalyst supports. The catalyst supports were dehydrated for 1 day at 150° C. and calcined for 1 hour at 1,100° C. This procedure gave silicon-free catalyst supports of a simple geometry; they have the following properties:

| - Lateral compressive strength | 304 N |
|---|---|
| - Water absorption | 0.270 ml/g |
| - BET surface area | 2.3 m²/g |
| - mean pore diameter (by the Hg pressure porosymmetry method) | 0.56 μm |
| - total pore volume (by the Hg pressure porosymmetry method) | 0.24 ml/g |

After impregnation and drying of the wagon wheels produced by the extrusion method as in Example 1, they were tested as in Example 1 in respect of their performance in the synthesis of N-vinylformamide from N-formylalanine nitrile.

| Conversion | 89 % |
|---|---|
| Selectivity | 91 % |
| Pressure drop | 3.5 mbar |
| Potassium loss | 26 % (not as silicate) |
| Heat transfer coefficient | 14 W/m²K |
| Radial thermal conductivity | 0.15 W/mK |
| Operating life | 600 h |

We claim:

1. An $SiO_2$-free $\alpha$-$Al_2O_3$ catalyst support which comprises at least 95% by weight of $\alpha$-$Al_2O_3$ and which is in the form of a hollow body wherein at least part of the outer walls of the hollow body is open.

2. The catalyst support defined in claim 1 which extends along a longitudinal axis and tapers along the longitudinal axis.

3. The catalyst support defined in claim 2, wherein the openings in the outer walls of the hollow body are oriented parallel to the longitudinal axis.

4. An $SiO_2$-free, $\alpha$-$Al_2O_3$-containing catalyst comprising the catalyst support defined in claim 1 and, applied thereto, at least one alkali metal compound or at least one alkaline earth metal compound or a mixture thereof.

5. An $SiO_2$-free, $\alpha$-$Al_2O_3$-containing catalyst comprising the catalyst support defined in claim 1 and at least one alkali metal compound or at least one alkaline earth metal compound or a mixture thereof, which catalyst is obtainable by a process comprising the steps of:

I) shaping a mixture comprising
   (A) a powder having an $\alpha$-$Al_2O_3$ content of at least 95% by weight and
   (B) a polymeric binder,
II) removing the polymeric binder (B),
III) presintering the shaped body obtained from step (II), and
IV) impregnating the shaped body obtained from step (III) with at least one solution of at least one alkali metal salt or at least one alkaline earth metal salt or a mixture thereof and subsequently drying the catalyst.

* * * * *